United States Patent [19]
Bajusz et al.

[11] 4,339,440
[45] Jul. 13, 1982

[54] ENKEPHALIN ANALOGS AND A PROCESS FOR THE PREPARATION THEREOF

[75] Inventors: Sándor Bajusz; András Rónai; József Székely, all of Budapest, Hungary

[73] Assignee: Richter Gedeon Vegyeszeti Gyar RT, Budapest, Hungary

[21] Appl. No.: 227,766

[22] Filed: Jan. 23, 1981

[30] Foreign Application Priority Data

Jan. 25, 1980 [HU] Hungary ............................. 155

[51] Int. Cl.$^3$ .................... A61K 37/00; C07C 103/52
[52] U.S. Cl. ............................... 424/177; 260/112.5 E
[58] Field of Search .................. 260/112.5 E; 424/177

[56] References Cited

U.S. PATENT DOCUMENTS 4,178,371 12/1979 Morgan ......................... 260/112.5 E Primary Examiner—Delbert R. Phillips
Attorney, Agent, or Firm—Karl F. Ross

[57] ABSTRACT

The invention relates to new enkephalin analogues of the general formula (I),

Tyr-X-Gly-Phe-Y   (I)

wherein
Tyr, Gly and Phe represent L-tyrosyl, glycyl and L-phenylalanyl residue, respectively,
X is glycyl residue or a D-α-aminocarboxylic acid residue with a lower alkyl, lower thioalkyl or phenyl-(lower)-alkyl side chain, and
Y is the residue of an L, D or DL-α-aminophosphonic acid or L, D or DL-α-aminosulfonic acid, each having a lower alkyl side chain, and salts thereof. These compounds are prepared according to the invention so that an L-, D- or DL-α-aminophosphonic acid or an L-, D- or DL-α-aminosulfonic acid, each bearing a lower alkyl side chain, is coupled in the proper order, as defined by formula (I), with the amino acids and/or peptide fragments each having a removable protecting group on the terminal amino group, the protecting group is split off from the terminal amino group, and the free peptide is isolated as such or in the form of its salt.

The new compounds according to the invention selectively modify the catecholamine content of the central nucleus of amygdala, thus they may specifically influence the following functions: food intake, emotionality, social behavior, learning and memory processes.

4 Claims, No Drawings

ENKEPHALIN ANALOGS AND A PROCESS FOR THE PREPARATION THEREOF

The invention relates to new enkephalin analogs of the general formula (I),

wherein

Tyr, Gly and Phe represent, in accordance with the literature [e.g. J. Biol. Chem. 247, 977 (1972)], an L-tyrosyl, a glycyl and an L-phenylalanyl residue, respectively, X is a glycyl residue or a D-α-aminocarboxylic acid residue with a lower alkyl, lower thioalkyl or phenyl-(lower)-alkyl side chain, and Y is the residue of an L, D or DL-α-aminophosphonic acid or L, D or DL-α-aminosulfonic acid, each having a lower alkyl side chain, and salts thereof. The invention also relates to pharmaceutical compositions which contain the above new compounds as active ingredients, as well as to a process for the preparation of the new compounds and pharmaceutical compositions.

It is known that the opiate (morphine-like) activities of methionine- and leucine-enkephalin, the two pentapeptides of the structures Tyr-Gly-Gly-Phe-Met and Tyr-Gly-Gly-Phe-Leu, isolated from the brain [Hughes et al.: Nature 258, 577 (1975)], can be increased by replacing certain amino acid residues thereof, primarily the 2-Gly and 5-Met or 5-Leu residues by other amino acid residues. Examples of these analogs are Tyr-D-Met-Gly-Phe-Pro-NH₂ (Belgian patent specification No. 858,453), Tyr-D-Ala-Gly-MePhe-Met(O)-ol [Roemer et al.: Nature 268, 547 (1977)] where MePhe stands for an N-methyl-L-phenylalanyl and Met(O)-ol stands for an L-methioninol-S-sulfoxide residue; and Tyr-D-Ala-Gly-Phe-D-Leu [Baxter et al.: Br. J. Pharmacol. 59, 455 (1977)].

By comparing the activities of natural opioid peptides and morphine or normorphine as measured on guinea pig ileum (GPI) and mouse vas deferens (MVD) preparations, the difference in the opioid character of the two compound types becomes clear [see e.g. Lord et al.: Nature 267, 495 (1977)]. Enkephalins are much more active on MVD than on GPI, whereas morphine shows higher activity on GPI. β-Endorphine of natural occurrence (a 31-membered polypeptide) is equally active on GPI and MVD, i.e. it reacts with the same potency with the opiate receptors in the two preparations. Of the analogs mentioned above Tyr-D-Ala-Gly-Phe-D-Leu is more active on MVD than on GPI, thus the character of its opiate activity resembles that of the enkephalins. Tyr-D-Met-Gly-Phe-Pro-NH₂ shows the same level of activity on both preparations, whereas Tyr-D-Ala-Gly-MePhe-Met(O)-ol is twice as active on GPI as on MVD. Thus the latter two analogs are closer in opiate properties to β-endorphine and morphine than to enkephalins.

The invention relates to enkephalin analogs which differ from the known ones primarily in the C-terminal moiety.

The literature reports certain dipeptides with a phosphonic acid group [Gilemor and McBridge: J. Pharm. Sci. 63, 1087 (1974)] or to sulfonic acid group [Shiba et al.: Bull. Chem. Soc. Japan, 50, 254 (1977)] in the place of the terminal carboxy group. A characteristic feature of these peptide analogs is that their acid group has a higher dissociation constant than the carboxy group of the real peptides, and the phosphonic acid derivatives contain a further —OH group with a dissociation constant lower than that of the carboxy group.

It has been found that by starting from aminophosphonic acids or aminosulfonic acids and applying methods generally known in the peptide chemistry, enkephalin analogs with terminal phosphonic acid or sulfonic acid groups can be synthesized.

It has also been found that the opiate activities of the resulting compounds having the formula (I), measured on MVD and GPI, and/or the ratio of the two activities (the high MVD/GPI potency ratio is characteristic of enkephalins) are greater than the same properties of the respective analogs with the same amino acid sequence but a terminal carboxy group. This relates particularly to the compounds in which group Y has L or DL configuration.

To prove the above statement, the opiate activities of some compounds having the formula (I) and those of the respective —COOH derivatives, determined on MVD according to Hughes et al. [Br. J. Pharmacol. 53, 371 (1975)] and on GPI according to Kosterlitz et al. [Br. J. Pharmacol. 39, 398 (1970)], are summarized in Table 1.

Notes to Table 1:
(a) The values determined on MVD or GPI preparates are related to the activity of Met-enkephalin determined on GPI (ID₅₀=183.5 nM) as unity.
(b) Nle: L-norleucyl, NleP: L-α-aminopentanephosphonic acid, NleS: L-α-aminopentanesulfonic acid.
(c) Control compound which contains a terminal —COOH group [S. Bajusz et al.: Acta Biochem. Biophys. Acad. Sci. Hung. 11, 305 (1976)]

TABLE 1

Opiate activities[a] of the compounds having the formula (I) and those of the respective substances with terminal —COOH groups

| Tyr—X—Gly—Phe—Y[b] | | MVD | GPI | MVD/GPI |
|---|---|---|---|---|
| — Gly — | NleP | 82.3 | 1.4 | 58.8 |
| — Gly — | NleS | 43.7 | 3.1 | 14.1 |
| — Gly — | Nle[c] | 8.9 | 0.5 | 17.8 |
| — D-Ala — | NleP | 941.0 | 11.2 | 84.0 |
| — D-Ala — | NleS | 327.7 | 7.8 | 42.0 |
| — D-Ala — | DL-NleS | 679.6 | 5.6 | 121.3 |
| — D-Ala — | Nle[c] | 183.5 | 2.8 | 65.5 |
| — D-Met — | NleP | 188.2 | 1.5 | 125.5 |
| — D-Met — | NleS | 374.5 | 9.9 | 37.8 |
| — D-Met — | Nle[c] | 305.8 | 4.8 | 63.7 |
| — D-Nle — | NleP | 774.3 | 4.9 | 158.0 |
| — D-Nle — | NleS | 873.8 | 21.6 | 40.45 |
| — D-Nle — | Nle[c] | 141.15 | 3.1 | 45.5 |

We have also found that the salts of compounds of the formula I formed with certain divalent cations, e.g. the copper and zinc salts of Tyr-D-Nle-Gly-Phe-NleS and Tyr-D-Nle-Gly-Phe-NleP, possess particularly high MVD/GPI potency ratios. The potency of these peptide salts is higher in MVD by at least one order of magnitude than the "zwitter-ion" form of the parent peptides or the sodium, potassium, magnesium and/or calcium salts thereof formed in the physiological salt solution used in the biological assay system. On the other hand, the copper and zinc ions attached to the peptides do not influence their potency in GPI.

According to our tests the compounds of the formula (I) selectively modify the catecholamine content of the central nucleus of amygdala. Since this group of nuclei has high enkephalin content and opiate receptor density and is not a part of the system which specifically influences pain sense, it can be assumed that the compounds of the formula (I) will specifically influence the following functions: food intake, emotionality, social behaviour, learning and memory processes, and endocrine and vegetative regulation systems.

We have demonstrated that peptides of the formula (I), e.g. Tyr-D-Ala-Gly-Phe-NleP and Tyr-D-Nle-Gly-Phe-D-NleS possess centrally mediated hypotensive effect in cats anesthetized with pentobarbital. In addition to the effects on the blood pressure and heart rate, the actions on the vasomotor reflex elicited by carotis occlusion, were also studied. The peptides in the dose applied produced hypotension accompanied by moderate bradycardia (see Table 2); both compounds inhibited the vasomotor reflex elicited by carotis occlusion. The maximal effects on blood pressure and heart rate could be detected 5–10 min after the administration, while the inhibition of vasomotor reflex culminated 20 min. after the intravenous injection of the peptides. The duration of the former effects was 20–25 min., while that of the latter was 40–60 min. Because none of these enkephalin analogs exerted analgesic action in rats, even in much higher doses (3–30 mg/kg i.v.) than it was applied in the present experiments, the centrally mediated hypotensive effect should be regarded as a selective one. It is noteworthy that the reference compound morphine was unable to elicit hypotension of similar magnitude produced by 0.1 mg/kg of peptides only in doses higher than 1.0 mg/kg (Table 2).

Remarks to Table 2:
(a) Cats of both sexes, weighing 3000–4000 g, anesthetized with 35 mg/kg pentobarbital, i.p.
(b) C.O.: Inhibition of vasomotor reflex elicited by carotis occlusion;
+ = inhibition is smaller than 50%,
+ + = inhibition is higher than 50%.

TABLE 2

The cardiovascular effects of Tyr—D-Ala—Gly—Phe—NleP and Tyr—D-Nle—Gly—Phe—D-NleS in anesthetized cats[a]

| Compound | Dose mg/kg i.v. | Fall in blood pressure mm Hg | Decrease of heart rate beat/min. | Inhibition of C.O.[b] |
|---|---|---|---|---|
| Tyr—D-Ala—Gly—Phe—NleP | 0.1 | 22.5 ± 1.4 | 21.3 ± 4.3 | + + |
| Tyr—D-Nle—Gly—Phe—D-NleS | 0.1 | 32.5 ± 1.4 | 25.0 ± 2.0 | + + |
| Morphine | 0.2 | 6.7 ± 2.1 | φ | φ |
|  | 1.0 | 16.7 ± 3.2 | 10.2 ± 2.3 | + |
|  | 5.0 | 33.6 ± 6.7 | 16.7 ± 3.5 | + + |

Furthermore, it was also established that Tyr-D-Ala-Gly-Phe-NleP, in the dose of 0.2–1.0 mg/kg i.v., produced a 2–5 fold increase of prolactin secretion in rats, which phenomenon indicates the ability of compounds of the formula (I) to influence endocrine regulation.

Finally, it has been found, unexpectedly, that the compounds of the formula (I) cannot be decomposed or hydrolyzed with carboxypeptidases. Thus, by replacing the terminal carboxy group of the peptides by a —PO₃H or —SO₃H group new compounds can be prepared which, apart from having resistance to carboxypeptidase, contain a terminal acid group. This enzyme resistance could be attained before only by changing the acidic character of the terminal amino acid, e.g. by converting the terminal carboxy group into an amide, ester or carbinol group. These modifications, as appears from the examination of enkephalin analogs, can cause significant changes in the original activity spectrum and biological character of the peptide.

The new compounds of the formula (I) can be prepared according to the invention in that an L-, D- or DL-α-aminophosphonic acid or an L-, D- or DL-α-aminosulfonic acid, each bearing a lower alkyl side chain, is coupled in a way known in the peptide chemistry, in the proper order, as defined by formula (I), with the amino acids and/or peptide fragments each having a removable protecting group on the terminal amino group, the protecting group is split off from the terminal amino group, and the free peptide is isolated as such or in the form of its salt.

According to a preferred method of the invention one proceeds as follows: A DL-α-aminophosphonic acid or DL-α-aminosulfonic acid, each having a lower alkyl side chain, is acylated in the presence of an equivalent amount of a base with a mixed anhydride prepared from an N-protected L-phenylalanine, the protecting group is removed, the resulting free diastereomeric dipeptides are separated from one another, any of the separated L-L or L-D dipeptide is coupled by the mixed anhydride or activated ester method with the appropriate tripeptide fragment which contains a removable protecting group, preferably a tert.-butoxycarbonyl group, on the terminal amino group, the protecting group is split off, and the resulting pentapeptide is isolated either as such or as its salt.

The invention is elucidated in detail by the aid of the following non-limited Examples. The $R_f$ values mentioned in the examples were determined by thin layer chromatography, using silica gel (Kieselgel G, produced by the firm Reanal, Budapest) as adsorbent and one of the following solvent mixtures as developing system:

| (1) | ethyl acetate-pyridine-acetic acid-water | 960:20:6:11 |
|---|---|---|
| (2) | ethyl acetate-pyridine-acetic acid-water | 240:20:6:11 |
| (3) | ethyl acetate-pyridine-acetic acid-water | 120:20:6:11 |
| (4) | ethyl acetate-pyridine-acetic acid-water | 80:20:6:11 |
| (5) | ethyl acetate-pyridine-acetic acid-water | 60:20:6:11 |
| (6) | ethyl acetate-pyridine-acetic acid-water | 30:20:6:11 |
| (7) | ethyl acetate-pyridine-formic acid-water | 60:20:6:5.5 |
| (8) | ethyl acetate-pyridine-formic acid-water | 30:20:6:5.5 |
| (9) | n-butanol-acetic acid-water | 4:1:1 |
| (10) | chloroform-methanol-acetic acid | 90:5:5 |
| (11) | chloroform-methanol-acetic acid | 3:1:1 |
| (12) | chloroform-n-hexane-acetic acid | 8:1:1 |
| (13) | chloroform-acetone | 9:1 |
| (14) | chloroform |  |

EXAMPLE 1

Preparation of L-tyrosyl-glycyl-glycyl-L-phenylalanyl-L-α-aminopentanephosphonic acid Step 1:

Benzyloxycarbonyl-DL-α-aminopentanephosphonic acid 45 g (300 mmoles) of benzylurethane are dissolved under stirring in a mixture of 60 ml of glacial acetic acid and 26.4 ml (300 mmoles) of phosphorous trichloride. The solution is cooled with ice water, and 52 ml (450 mmoles) of n-valeraldehyde are added to the stirred solution at a temperature not exceeding 10° C. The reaction mixture is placed under vacuum ($3-4 \times 10^4$ Pa). The temperature of the cooled solution decreases first to 2°–3° C., then hydrochloric acid starts to evolve and the temperature of the mixture raises to 30°–40° C. At this stage the cooling bath is removed and the mixture is maintained at 65°–75° C. for 2 hours. The reaction mixture gradually thickens upon heating, and finally solidifies. After 3–4 hours 18 ml of water are added to the mixture, and the resulting mixture is allowed to stand at room temperature under atmospheric pressure overnight. The resulting two-phase liquid is evaporated under reduced pressure to remove acetic acid, and the residue is dissolved in a mixture of 500 ml of ethyl acetate and 300 ml of water. The organic phase is washed successively with water (2×100 ml), 1 n aqueous hydrochloric acid (2–100 ml) and 1 n aqueous sodium hydroxide solution (3×150 ml). The sodium hydroxide solutions are combined, washed with 50 ml of ethyl acetate, then acidified to pH=1 with 5 n aqueous sulfuric acid, and the acidic solution is extracted three times with 200 ml of ethyl acetate, each. The ethyl acetate solutions are combined, dried over anhydrous sodium sulfate and evaporated under reduced pressure. The residue is dissolved in 500 ml of diisopropyl ether, and 60 ml of dicyclohexyl amine are added. The separated crystals are filtered off, washed with diisopropyl ether and dried in air. The product is dissolved in 150 ml of hot ethanol, the solution is cooled to 40°–50° C., and 800 ml of diisopropyl ether are added. The separated crystals are filtered off, washed with diisopropyl ether and dried in air. The resulting salt (97 g, m.p.: 147°–149° C.) is dissolved in a mixture of 500 ml of ethyl acetate and 300 ml of 5 n aqueous sulfuric acid, the ethyl acetate phase is separated, washed twice with 300 ml of 5 n aqueous sulfuric acid, each, dried over anhydrous sodium sulfate, and finally evaporated under reduced pressure. The residue is crystallized from petroleum ether. 54.3 g (60%) of benzyloxycarbonyl-DL-α-aminopentanephosphonic acid are obtained; m.p.: 98°–100° C., $R_f{}^5 = 0.45$–0.55.

Step 2: DL-α-Aminopentanephosphonic acid 45.3 g (150 mmoles) of benzyloxycarbonyl-DL-α-aminopentanephosphonic acid, prepared as described in Step 1, are suspended in 500 ml of water, 42 ml (300 mmoles) of triethyl amine are added, and the mixture is hydrogenated in the presence of palladium-on-carbon catalyst. At the end of the reaction the catalyst is filtered off, washed with water, and the aqueous solutions are evaporated under reduced pressure. The residue is dissolved in 150 ml of hot 1 n aqueous acetic acid solution, the solution is decolourized with carbon, filtered, and the filtrate is diluted with 900 ml of ethanol. The mixture is allowed to stand at 0° C. The separated crystals are filtered off, washed with ethanol, and dried in a vacuum desiccator. 23.1 g (92%) of DL-α-aminopentanephosphonic acid are obtained; m.p.: 275°–278° C., $R_f{}^5 = 0.0$–0.1, $R_f{}^6 = 0.23$–0.33.

Step 3: L-Phenylalanyl-D-α-aminopentanephosphonic acid 39.8 g (150 mmoles) of tert.-butoxycarbonyl-L-phenylalanine and 16.7 ml (150 mmoles) of N-methylmorpholine are dissolved in a mixture of 100 ml of dioxane and 100 ml of tetrahydrofuran. The solution is cooled to −10° C., and 19.2 ml (145 mmoles) of isobutyl chloroformate are added with stirring. After 10 minutes a solution of 16.7 g (100 mmoles) of DL-α-aminopentanephosphonic acid, prepared as described in Step 2, in 55 ml of a 4 n aqueous sodium hydroxide solution is added to the stirred mixture. The reaction mixture is stirred at −5° to −10° C. for 5 hours, then concentrated to about 70 ml under reduced pressure. The residue is dissolved in a mixture of 500 ml of 0.5 n aqueous sulfuric acid and 500 ml of ethyl acetate. The aqueous phase is separated, washed twice with 100 ml of ethyl acetate, each, then the ethyl acetate solutions are combined and extracted five times with 100 ml of 20% aqueous pyridine, each. The ethyl acetate solution is washed with 0.5 n aqueous sulfuric acid, dried over anhydrous sodium sulfate and evaporated. Thus 16 g (60 mmoles) of non-reacted tert.-butoxycarbonyl-L-phenylalanine are recovered. The aqueous solutions are combined and evaporated under reduced pressure. The residue is dissolved in 200 ml of ethyl acetate containing a sufficient amount of 0.5 n aqueous sulfuric acid to adjust the pH of the aqueous phase to 2. The aqueous phase is separated, washed twice with 50 ml of ethyl acetate, each, the ethyl acetate solutions are combined, washed with 50 ml of water, and then evaporated under reduced pressure. A mixture of 10 ml of ethanol and 40 ml of benzene is added to the residue, and the mixture is evaporated. The residue is dissolved in 50 ml of trifluoroacetic acid. The solution is allowed to stand for 30 minutes, then evaporated, the residue is triturated with ether, filtered, and the solid is dried in a vacuum desiccator over potassium hydroxide. The product is dissolved in 70 ml of acetic acid at 40°–50° C., 125 ml of warm (40°–50° C.) water are added, and the mixture is allowed to stand at room temperature overnight. The separated crystals are filtered off and washed thrice with 10 ml of 30% aqueous acetic acid, each. The acidic mother liquor and wash are stored for further processing (see Step 4 of Example 1). The crystalline product is dried in a vacuum desiccator over potassium hydroxide. 11.0 g (35 mmoles, 70%) of L-phenylalanyl-D-α-aminopentanephosphonic acid are obtained; m.p.: 262° C., $[\alpha]_D{}^{20} = +68.9°$ (c=1%, in 1 n aqueous sodium hydroxide solution), $R_f{}^6 = 0.45$–0.50.

Step 4: L-Phenylalanyl-L-α-aminopentanephosphonic acid

The acetic acid mother liquor and washings obtained in the crystallization step described in Step 3 are combined and evaporated under reduced pressure. 50 ml of dioxane are added to the oily-crystalline residue, the mixture is evaporated, and this operation is repeated. The residue is suspended in 50 ml of dioxane, the solid is filtered off, washed with dioxane and then with ether, finally dried in a vacuum desiccator over potassium hydroxide. 10.9 g (34.8 mmoles, 69.5%) of L-phenylalanyl-L-α-aminopentanephosphonic acid are obtained; m.p.: 251°–253° C., $[\alpha]_D{}^{20} = -53.1°$ (c=1%, in 1 n aqueous sodium hydroxide solution), $R_f{}^6 = 0.48$–0.53.

Step 5: tert.-Butoxycarbonyl-glycyl-glycine benzyl ester 14.2 g (42 mmoles) of glycine benzyl ester p-toluenesulfonate are dissolved in 100 ml of dimethyl formamide, 4.6 ml (42 mmoles) of N-methylmorpholine and 14.2 g (40 mmoles) of tert.-butoxycarbonyl-glycine 2,4,5-trichlorophenyl ester are added, and the mixture is stirred at room temperature overnight. The reaction mixture is evaporated, and the residue is dissolved in a mixture of 150 ml of ethyl acetate and 50 ml of water. The ethyl acetate phase is washed twice with 30 ml of ice-cooled 1 n aqueous hydrochloric acid, each, and then with water, dried over sodium sulfate and evaporated. The residue is triturated with a 1:1 mixture of diisopropyl ether and petroleum ether, filtered, the solid is washed with the same solvent mixture and dried in a desiccator. 11.0 g (82.8%) of tert.-butoxycarbonyl-glycyl-glycine benzyl ester are obtained; m.p.: 83° C., $R_f^{14}=0.1$–$0.2$.

Step 6: tert.-Butoxycarbonyl-L-tyrosyl-glycyl-glycine 10.15 g (31.5 mmoles) of the protected dipeptide ester prepared as described in Step 5 are dissolved in 100 ml of ethyl acetate containing 11–15% of hydrochloric acid. The mixture is allowed to stand for 0.5 hours, then evaporated under reduced pressure, and the residue is dried in a vacuum desiccator over potassium hydroxide. The resulting product (7.8 g, $R_f^3=0.1$–$0.2$) is dissolved in 35 ml of dimethyl formamide, 3.4 ml (30.13 mmoles) of N-methylmorpholine and 15.1 g (30 mmoles) of tert.-butoxycarbonyl-L-tyrosine pentachlorophenyl ester are added, and the mixture is allowed to stand for 16–20 hours. In the first two hours of the reaction 3.3 ml (30 mmoles) of N-methylmorpholine are added to the mixture in five portions. The solution is evaporated under reduced pressure, the residue is dissolved in a mixture of 250 ml of ethyl acetate and 50 ml of water, the ethyl acetate phase is washed successively with 5% aqueous sodium hydrocarbonate solution (2×50 ml), water (2×50 ml), ice-cooled 1 n aqueous hydrochloric acid (2×50 ml) and water, dried over sodium sulfate, decolourized with carbon, filtered, and the filtrate is evaporated under reduced pressure. The residue is triturated with diisopropyl ether, the solid is filtered off, washed with diisopropyl ether and dried in a vacuum desiccator. The resulting protected tripeptide ester, $R^{10}=0.65$–$0.75$, is dissolved in 150 ml of methanol, and the mixture is hydrogenated in the presence of palladium-on-carbon catalyst. At the end of the reaction the catalyst is filtered off, the methanol solution is evaporated under reduced pressure, and the residue is triturated with a 1:1 mixture of diethyl ether and diisopropyl ether. The solid is filtered off and dried in a vacuum desiccator. 8.35 g (70.3%) of tert.-butoxycarbonyl-L-tyrosyl-glycyl-glycine are obtained; m.p.: 92°–94° C., $R_f^3=0.2$–$0.3$.

Step 7:
L-Tyrosyl-glycyl-glycyl-L-phenylalanyl-L-α-aminopentanephosphonic acid 0.95 g (2.4 mmoles) of the protected tripeptide prepared as described in Step 6 and 0.27 ml (2.4 mmoles) of N-methylmorpholine are dissolved in 5 ml of dimethyl formamide, and 0.31 ml (2.4 mmoles) of isobutyl chloroformate are added to the stirred solution at −10° C. After 10 minutes a mixture of 0.63 g (2 mmoles) of L-phenylalanyl-L-α-aminopentanephosphonic acid, prepared as described in Step 4 of Example 1, 0.56 ml (4 mmoles) of triethyl amine, 4 ml of dimethyl formamide and 0.5 ml of water is introduced. The reaction mixture is stirred at −5° to −10° C. for 3–4 hours, then evaporated under reduced pressure. The residue is dissolved in 20 ml of a 5% aqueous pyridine solution, and a solution of 0.3 g (2.3 mmoles) of calcium chloride hydrate in 5 ml of water is added. The separated precipitate is filtered off, washed five times with 5 ml of water, each, and then 10 ml of a 1 n aqueous sulfuric acid solution and 30 ml of ethyl acetate are added. The mixture is stirred thoroughly, the separated calcium sulfate is filtered off, and the phases of the filtrate are separated. The aqueous phase is washed twice with 10 ml of ethyl acetate, each, the ethyl acetate solutions are combined, washed twice with 10 ml of water, each, and evaporated under reduced pressure. The residue is dissolved in 10 ml of trifluoroacetic acid, and the solution is allowed to stand for 30 minutes. The solution is evaporated under reduced pressure, 10 ml of acetic acid are distilled off from the residue, this operation is repeated, then the product is dried in a vacuum desiccator over potassium hydroxide. The product is triturated with 5 ml of water, filtered, washed thrice with 3 ml of water, each, and dried in a vacuum desiccator over potassium hydroxide. 0.85 g (72%) of L-tyrosyl-glycyl-glycyl-L-phenylalanyl-L-α-aminopentanephosphonic acid are obtained; m.p.: 203°–205° C., $[\alpha]_D^{20}=-8°$ (c=1%, in 1 n aqueous sodium hydroxide solution), $R_f^5=0.30$–$0.35$.

EXAMPLE 2

Preparation of
L-tyrosyl-glycyl-glycyl-L-phenylalanyl-L-α-aminopentanesulfonic acid Step 1: DL-α-Aminopentanesulfonic acid 52 g (500 mmoles) of sodium bisulfite are dissolved in 250 ml of warm water, 53.6 ml (510 mmoles) of n-valeraldehyde are added, and the resulting orange-red mixture is stirred on a steam bath until it turns colorless. The solution is cooled to room temperature, 400 ml of concentrated aqueous ammonia are added, the mixture is stirred at room temperature for one hour, and then allowed to stand in a refrigerator overnight. The reaction mixture is washed with 100 ml of diethyl ether, decolourized with carbon, filtered, and the pH of the filtrate is adjusted to 3 with concentrated aqueous hydrochloric acid under cooling. The separated crystalline substance is filtered off, washed with water and diethyl ether, and dried in a vacuum desiccator. 47.6 g (56.8%) of DL-α-aminopentanesulfonic acid are obtained; m.p.: 142° C., $R_f^9=0.3$–$0.4$.

Step 2:
Benzyloxycarbonyl-L-phenylalanyl-DL-α-aminopentanesulfonic acid 101.8 g (340 mmoles) of benzyloxycarbonyl-L-phenylalanine are dissolved in 950 ml of dimethyl formamide, the solution is cooled to −10° C., and 37.8 ml (340 mmoles) of N-methylmorpholine and 41.5 ml (340 mmoles) of pivaloyl chloride are added to the stirred solution at the same temperature. After 10 minutes of stirring the mixture is cooled to −30° C., and 51.7 g (309 mmoles) of DL-α-aminopentanesulfonic acid and 43.3 ml (309 mmoles) of triethyl amine are added to the stirred mixture at the same temperature. Stirring is continued for 10 minutes at −10° C., then for one hour at 0° C., thereafter the mixture is stirred at room temperature overnight. The reaction mixture is evaporated under reduced pressure, and the residue is dissolved in 1500 ml of water. The aqueous solution is washed thrice with 300 ml of diethyl ether, each, then acidified to pH=2 with concentrated aqueous hydrochloric acid under ice cooling, and the acidic mixture is extracted thrice with 300 ml of n-butanol saturated with water, each. The butanol solutions are combined, washed with 50 ml of water saturated with n-butanol, decolored with carbon, filtered, and the filtrate is evaporated under reduced pressure. 82.6 g (85%) of benzyloxycarbonyl-L-phenylalanyl-DL-α-aminopentanesulfonic acid are obtained; $R_f^3=0.2$–$0.3$.

Step 3: L-Phenylalanyl-D-α-aminopentanesulfonic acid 82.6 g (262.7 mmoles) of the protected dipeptide obtained as described in Step 2 are dissolved in 3000 ml of methanol, and the mixture is hydrogenated in the presence of palladium-on-carbon catalyst. At the end of the reaction (the $R_f^2$ value of the substance in solution is 0.05–0.15) the separated substance and the catalyst are filtered off and washed four times with 300 ml of methanol, each. The methanol solutions are combined and stored for further processing. The filter cake, which contains the catalyst as contamination, is suspended in 300 ml of 50% aqueous dimethyl formamide, the suspension is heated to 70°–80° C., and the warm mixture is filtered. The catalyst is washed twice with 50 ml of warm 50% aqueous dimethyl formamide, each. The aqueous dimethylformamide solutions are combined and evaporated under reduced pressure. The crystalline residue is suspended in methanol, filtered, the solid is washed with methanol and diethyl ether, then dried in a vacuum desiccator. 34.5 g (83%) of L-phenylanalyl-D-α-aminopentanesulfonic acid are obtained; m.p.: 284°–285° C., $[\alpha]_D^{20} = +127.5°$ (c=1%, in 1 n aqueous sodium hydroxide solution).

Step 4: L-Phenylalanyl-L-α-aminopentanesulfonic acid

The methanolic solution obtained in Step 3 is evaporated under reduced pressure. The crystalline residue is suspended in 100 ml of acetone, filtered, washed with acetone, and dried in a vacuum desiccator. The resulting product, weighing 34.6 g, is suspended in 700 ml of 80% aqueous ethanol, the mixture is heated to boiling, the insolubles are filtered off, and the filtrate is allowed to stand in a refrigerator overnight. The separated crystals are filtered off, washed with cold 80% aqueous ethanol, and dried in a vacuum desiccator. This crystallization step is repeated twice more, utilizing 600 ml and 500 ml of 80% aqueous ethanol, respectively. 20.7 g (50%) of L-phenylalanyl-L-α-aminopentanesulfonic acid are obtained; m.p.: 220° C., $R_f^1 = 0.52$–0.60, $R_f^{11} = 0.4$–0.5, $[\alpha]_D^{20} = -73.1°$ (c=1%, in 1 n aqueous sodium hydroxide solution).

Step 5: tert.-Butoxycarbonyl-L-tyrosyl-glycyl-glycine pentachlorophenyl ester 6.0 g (15 mmoles) of the protected tripeptide prepared as described in Step 6 of Example 1 and 4.3 g (16 mmoles) of pentachlorophenol are dissolved in 50 ml of dimethyl formamide, and the solution is cooled to about 5° C. with ice water. 3.4 g (16.5 mmoles) of dicyclohexyl carbodiimide are added, and the mixture is stirred under cooling for one hour and then at room temperature overnight. The separated dicyclohexyl urea is filtered off, washed with dimethyl formamide, the dimethyl formamide solutions are combined and evaporated. The residue is suspended in 100 ml of ethanol, the suspension is heated on a steam bath for 0.5 hours, then cooled with ice water. The solid is filtered off, washed with cold ethanol and dried in a vacuum desiccator. 6.7 g (69%) of tert.-butoxycarbonyl-L-tyrosylglycyl-glycine pentachlorophenyl ester are obtained; m.p.: 186° C., $R_f^{10} = 0.6$–0.7.

Step 6:
tert.-Butoxycarbonyl-L-tyrosyl-glycyl-glycyl-L-phenylalanyl-L-α-aminopentanesulfonic acid N-methylmorpholine salt 0.95 g (3 mmoles) of the dipeptide prepared as described in Step 4 are suspended in 10 ml of dimethyl formamide, 0.35 ml (3 mmoles) of N-methylmorpholine and 2.0 g (3.15 mmoles) of the protected tripeptide ester prepared as described in Step 5 are added, and the mixture is stirred for 16–20 hours. In the first 2 hours of stirring further 0.35 ml (3.15 mmoles) of N-methylmorpholine are added to the mixture in five portions. The reaction mixture is evaporated under reduced pressure, and the residue is dissolved in a mixture of 20 ml of ethyl acetate and 60 ml of water. The aqueous phase is washed twice with 20 ml of ethyl acetate, each, decolored with carbon, filtered, and the filtrate is evaporated under reduced pressure. The residue is dissolved in 20 ml of ethanol, and the solution is evaporated. The residue is triturated with diethyl ether under cooling, the solid is filtered off, washed with diethyl ether and dried in a vacuum desiccator. 1.82 g (76.5%) of tert.-butoxycarbonyl-L-tyrosyl-glycyl-glycyl-L-phenylalanyl-L-α-aminopentanesulfonic acid N-methylmorpholine salt are obtained; m.p.: 130° C., $R_f^7 = 0.25$–0.30, $[\alpha]_D^{20} = -24.8°$ (c=1%, in dimethyl formamide).

Step 7:
L-Tyrosyl-glycyl-glycyl-L-phenylalanyl-L-α-aminopentanesulfonic acid 1.4 g (1.75 mmoles) of the protected pentapeptide salt prepared as described in Step 6 are dissolved in 10 ml of trifluoroacetic acid, the solution is allowed to stand at room temperature for 0.5 hours, and then evaporated under reduced pressure. The residue is triturated with diethyl ether, the solid is filtered off, washed successively with diethyl ether, ethyl acetate and diethyl ether again, and dried in a vacuum desiccator. 1.05 g (99%) of L-tyrosyl-glycyl-glycyl-L-phenylalanyl-L-α-aminopentanesulfonic acid are obtained; m.p.: 192°–194° C., $R_f^5 = 0.20$–0.35, $R_f^8 = 0.35$–0.45, $[\alpha]_D^{20} = +6.01°$ (c=1%, in 90% acetic acid).

EXAMPLE 3

Preparation of
L-tyrosyl-D-alanyl-glycyl-L-phenylalanyl-L-α-aminopentanephosphonic acid One proceeds as described in Step 7 of Example 1 with the difference that 0.98 g (2.4 mmoles) of tert.-butoxycarbonyl-L-tyrosyl-D-alanyl-glycine [Pless et al.: Helv. Chim. Acta 62, 398 (1979)] and 0.63 g (2 mmoles) of L-phenylalanyl-L-α-aminopentanephosphonic acid prepared as described in Step 4 of Example 1 are used as starting substances. 0.85 g (70%) of L-tyrosyl-D-alanyl-glycyl-L-phenylalanyl-L-α-aminopentanephosphonic acid are obtained; m.p.: 255°–257° C., $[\alpha]_D^{20} = +24.5°$ (c=1%, in 1 n aqueous sodium hydroxide solution), $R_f^5 = 0.30$–0.40.

EXAMPLE 4

Preparation of
L-tyrosyl-D-alanyl-glycyl-L-phenylalanyl-L-α-aminopentanesulfonic acid Step 1: tert.-Butoxycarbonyl-L-tyrosyl-D-alanylglycine pentachlorophenyl ester 6.15 g (15 mmoles) of tert.-butoxycarbonyl-L-tyrosyl-D-alanyl-glycine [Pless et al.: Helv. Chem. Acta 62, 398 (1979)] are converted into active ester as described in Step 5 of Example 2. 7.6 g (76.6%) of tert.-butoxycarbonyl-L-tyrosyl-D-alanyl-glycine pentachlorophenyl ester are obtained; m.p.: 222° C., $R_f^{12}=0.1-0.2$.

Step 2: Triethyl amine salt of
tert.-butoxycarbonyl-L-tyrosyl-D-alanyl-glycyl-L-phenylalanyl-L-α-aminopentanesulfonic acid 0.95 g (3 mmoles) of the dipeptide prepared as described in Step 4 of Example 2 are condensed with 2.1 g (3.15 mmoles) of the protected tripeptide ester prepared as described in Example 4, Step 1. The reaction is performed as described in Step 6 of Example 2 with the difference that 0.4 ml and 0.45 ml of triethyl amine are applied as tertiary base. 1.99 g (82.2%) of tert.-butoxycarbonyl-L-tyrosyl-D-alanyl-glycyl-L-phenylalanyl-L-α-aminopentanesulfonic acid triethylamine salt are obtained; m.p.: 125° C., $R_f^5=0.35-0.45$, $[\alpha]_D^{20}=-25.1°$ (c=1%, in dimethyl formamide).

Step 3:
L-Tyrosyl-D-alanyl-glycyl-L-phenylalanyl-L-α-aminopentanesulfonic acid 1.4 g (1.75 mmoles) of the protected pentapeptide salt prepared as described in Step 2 of Example 4 are deprotected as described in Step 7 of Example 2 with the difference that the precipitate is also washed with 10 ml of water. 0.75 g (70.4%) of L-tyrosyl-D-alanyl-glycyl-L-phenylalanyl-L-α-aminopentanesulfonic acid are obtained; m.p.: 235°-240° C., $R_f^5=0.35-0.45$, $R_f^7=0.1-0.2$, $[\alpha]_D^{20}=+5.9°$ (c=1%, in 80% acetic acid).

EXAMPLE 5

Preparation of
L-tyrosyl-D-methionyl-glycyl-L-phenylalanyl-L-α-aminopentanephosphonic acid Step 1: tert.-Butoxycarbonyl-D-methionyl-glycyl benzyl ester 12.9 g (30 mmoles) of tert.-butoxycarbonyl-D-methionine dicyclohexylamine salt and 0.35 ml (3 mmoles) of N-methylmorpholine are dissolved in 120 ml of dimethyl formamide, and the solution is cooled to −10° C. 3.95 ml (30 mmoles) of isobutyl chloroformate are added to the stirred solution at the same temperature. After 10 minutes the mixture is cooled to −20° C., and a −20° C. solution of 11.15 g (33 mmoles) of glycine benzyl ester p-toluenesulfonate and 3.7 ml (33 mmoles) of N-methylmorpholine in 50 ml of dimethyl formamide is added. The reaction mixture is stirred at −10° C. for 10 minutes, at 0° C. for one hour and then at room temperature overnight. Thereafter the mixture is concentrated under reduced pressure, the residue is dissolved in a mixture of 200 ml of ethyl acetate and 100 ml of 0.01 n aqueous sulfuric acid, the ethyl acetate phase is separated, washed twice with 30 ml of 0.01 n aqueous sulfuric acid and twice with 30 ml of water, each, dried, decolourized with carbon, and evaporated under reduced pressure. The residue is triturated with petroleum ether, the solid is filtered off, washed with petroleum ether and dried in a vacuum desiccator. 11.3 g (94.8%) of tert.-butoxycarbonyl-D-methionyl-glycyl benzyl ester are obtained; m.p.: 67°-68° C., $R_f^1=0.8-0.9$, $R_f^{14}=0.35-0.45$, $[\alpha]_D^{20}=+10.4°$ (c=1%, in dimethyl formamide).

Step 2:
tert.-Butoxycarbonyl-L-tyrosyl-D-methionylglycine 9.9 g (25 mmoles) of the protected dipeptide ester obtained as described in Step 1 above are dissolved in 50 ml of ethyl acetate containing 11-15% of hydrochloric acid, and after 30 minutes of standing the mixture is evaporated under reduced pressure. The residue is dried in a vacuum desiccator over potassium hydroxide. The resulting product, $R_f^2=0.15-0.25$, is dissolved in 50 ml of dimethyl formamide, and 2.8 ml (25 mmoles) of N-methylmorpholine and 14.55 g (27.5 mmoles) of tert.-butoxycarbonyl-L-tyrosine pentachlorophenyl ester are added. The reaction mixture is stirred overnight. In the first two hours of stirring further 3.05 ml (27.5 mmoles) of N-methylmorpholine are added to the mixture in five portions. The reaction mixture is evaporated under reduced pressure, and the residue is dissolved in a mixture of 150 ml of ethyl acetate and 50 ml of water. The ethyl acetate phase is washed successively with 5% aqueous sodium hydrocarbonate solution (3×30 ml), water (3×30 ml), 0.1 n aqueous hydrochloric acid cooled with ice water (3×30 ml) and then with water (3×30 ml) again, dried over sodium sulfate, decolored with carbon, filtered, and the filtrate is evaporated under reduced pressure. The residue, $R_f^{12}=0.1-0.2$, is dissolved in 100 ml of methanol, and 30 ml of water and 54 ml of 1 n aqueous sodium hydroxide solution are added. The reaction mixture is allowed to stand at room temperature for one day. Thereafter methanol is distilled off under reduced pressure, the aqueous solution is shaken thrice with 20 ml of ethyl acetate, each, and acidified to pH=3 with solid citric acid. The separated substance is filtered off, washed with water and dried in a vacuum desiccator. 7.6 g (64.7%) of tert.-butoxycarbonyl-L-tyrosyl-D-methionyl-glycine are obtained; m.p.: 194° C., $R_f^2=0.24-0.34$, $[\alpha]_D^{20}=+11.44°$ (c=1%, in dimethyl formamide).

Step 3:
L-Tyrosyl-D-methionyl-glycyl-L-phenylalanyl-L-α-aminopentanephosphonic acid One proceeds as described in Step 7 of Example 1 with the difference that 1.13 g (2.4 mmoles) of tert.-butoxycarbonyl-L-tyrosyl-D-methionyl-glycine, prepared according to Step 2 of Example 5, and 0.63 g (2 mmoles) of L-phenylalanyl-L-α-aminopentanephosphonic acid, prepared according to Step 4 of Example 1, are used as starting substances. 0.9 g (70%) of L-tyrosyl-D-methionyl-glycyl-L-phenylalanyl-L-α-aminopentanephosphonic acid are obtained; m.p.: 193°-195° C., $[\alpha]_D^{20}=+15.6°$ (c=1%, in 1 n aqueous sodium hydroxide solution), $R_f^5=0.35-0.40$.

EXAMPLE 6

Preparation of
L-tyrosyl-D-methionyl-glycyl-L-phenylalanyl-L-α-aminopentanesulfonic acid Step 1:
tert.-Butoxycarbonyl-L-tyrosyl-D-methionylglycine pentachlorophenyl ester 7.05 g (15 mmoles) of the protected tripeptide prepared as described in Step 2 of Example 5 are converted into the active ester as described in Step 5 of Example 2, with the difference that the product is purified by triturating it with diisopropyl ether. 8.66 g (80.4%) of tert.-butoxycarbonyl-L-tyrosyl-D-methionyl-glycine pentachlorophenyl ester are obtained; m.p.: 175°–176° C., $R_f^{12} = 0.25$–$0.35$, $[\alpha]_D^{20} = +21.7°$ (c=1%, in dimethyl formamide).

Step 2:
tert.-Butoxycarbonyl-L-tyrosyl-D-methionylglycyl-L-phenylalanyl-L-α-aminopentanesulfonic acid N-methylmorpholine salt 2.26 g (3.15 mmoles) of the protected tripeptide ester prepared as described in Step 1 above are condensed with 0.95 g (3 mmoles) of the dipeptide prepared according to Step 4 of Example 2. The reaction is performed as described in Step 6 of Example 2 to obtain 1.73 g (66.5%) of tert.-butoxycarbonyl-L-tyrosyl-D-methionyl-glycyl-L-phenylalanyl-L-α-aminopentanesulfonic acid N-methylmorpholine salt; m.p.: 124°–127° C., $R_f^5 = 0.35$–$0.45$, $[\alpha]_D^{20} = -15°$ (c=1%, in dimethyl formamide).

Step 3:
L-Tyrosyl-D-methionyl-glycyl-L-phenylalanyl-L-α-aminopentanesulfonic acid 1.5 g (1.75 mmoles) of the protected pentapeptide salt prepared as described in Step 2 above are processed further according to the method of Example 2, Step 7, with the difference that the product is also washed twice with 10 ml of hot water, each. 0.78 g (66.7%) of L-tyrosyl-D-methionyl-glycyl-L-phenylalanyl-L-α-aminopentanesulfonic acid are obtained; m.p.: 200°–201° C., $R_f^5 = 0.5$–$0.6$, $R_f^7 = 0.2$–$0.3$, $[\alpha]_D^{20} = -20°$ (c=1%, in trifluoroacetic acid).

EXAMPLE 7

Preparation of
L-tyrosyl-D-norleucyl-glycyl-L-phenylalanyl-L-α-aminopentanephosphonic acid Step 1: tert.-Butoxycarbonyl-D-norleucyl-glycine benzyl ester 11.57 g (50 mmoles) of tert.-butoxycarbonyl-D-norleucine and 5.6 ml (50 mmoles) of N-methylmorpholine are dissolved in 50 ml of dimethyl formamide. The solution is cooled to −10° C., and 6.6 ml (50 mmoles) of isobutyl chloroformate are added with stirring. After 10 minutes the mixture is cooled to −20° C., and a solution of 18.6 g (55 mmoles) of glycine benzyl ester p-toluolsulfonate and 6.1 ml (55 mmoles) of N-methylmorpholine in 80 ml of dimethyl formamide, cooled to −20° C., is added. The reaction mixture is stirred at −10° C. for 10 minutes, at 0° C. for one hour and then at room temperature overnight. The mixture is filtered, and the filtrate is evaporated under reduced pressure. The residue is dissolved in a mixture of 300 ml of ethyl acetate and 100 ml of water. The ethyl acetate phase is separated, washed successively with 5% aqueous sodium hydrocarbonate solution (2×60 ml), water (2×60 ml), 1 n hydrochloric acid cooled with ice water (2×60 ml) and water (2×60 ml) again, dried over sodium sulfate, decolourized with carbon, filtered, and the filtrate is evaporated under reduced pressure. The crystalline residue is triturated with diisopropyl ether, the solid is filtered off, washed with diisopropyl ether and dried. 14.65 g (76.9%) of tert.-butoxycarbonyl-D-norleucyl-glycine benzyl ester are obtained; m.p.: 85°–86° C., $R_f^{13} = 0.75$–$0.85$, $[\alpha]_D^{20} = +12.2°$ (c=1%, in dimethyl formamide).

Step 2:
tert.-Butoxycarbonyl-L-tyrosyl-D-norleucylglycine benzyl ester

One proceeds as described in Step 2 of Example 5 with the difference that 14.2 g (37.5 mmoles) of the protected dipeptide ester prepared according to Step 1 above and 21.85 g (41.25 mmoles) of tert.-butoxycarbonyl-L-tyrosine pentachlorophenyl ester are used as starting substance, and 4.2 ml and 4.6 ml of N-methylmorpholine are added to the mixture. 15.44 g (76%) of tert.-butoxycarbonyl-L-tyrosyl-D-norleucyl-glycine benzyl ester are obtained; m.p.: 122° C., $R_f^{12} = 0.25$–$0.35$, $[\alpha]_D^{20} = +6°$ (c=1%, in dimethyl formamide).

Step 3:
tert.-Butoxycarbonyl-L-tyrosyl-D-norleucylglycine 14.9 g (27.5 mmoles) of the protected tripeptide ester obtained in Step 2 above are dissolved in 300 ml of methanol, 55 ml of a 1 n sodium hydroxide solution are added, and the mixture is allowed to stand at room temperature for 3 hours. Thereafter methanol is distilled off under reduced pressure, the aqueous solution is shaken thrice with 15 ml of ethyl acetate, each, and acidified to pH=3 with solid citric acid. The separated substance is filtered off, washed with water and dried in a vacuum desiccator. 8.1 g (65%) of tert.-butoxycarbonyl-L-tyrosyl-D-norleucyl-glycine are obtained; m.p.: 174°–175° C., $R_f^2 = 0.35$–$0.45$, $[\alpha]_D^{20} = +2.0°$ (c=1%, in dimethyl formamide).

Step 4:
L-Tyrosyl-D-norleucyl-glycyl-L-phenylalanyl-L-α-aminopentanephosphonic acid One proceeds as described in Step 7 of Example 1 with the difference that 1.08 g (2.4 mmoles) of tert.-butoxycarbonyl-L-tyrosyl-D-norleucyl-glycine obtained in Step 3 above and 0.63 g (2 mmoles) of L-phenylalanyl-L-α-aminopentanephosphonic acid, prepared as described in Step 4 of Example 1, are used as starting substances. 0.85 g (65%) of L-tyrosyl-D-norleucylglycyl-phenylalanyl-L-α-aminopentanephosphonic acid are obtained; m.p.: 196°–198° C., $[\alpha]_D^{20} = +8°$ (c=1%, in 1 n aqueous sodium hydroxide solution), $R_f^5 = 0.35$–$0.40$.

EXAMPLE 8

Preparation of
L-tyrosyl-D-norleucyl-glycyl-L-phenylalanyl-L-α-aminopentanesulfonic acid

Step 1:
tert.-Butoxycarbonyl-L-tyrosyl-D-norleucylglycine pentachlorophenyl ester 6.8 g (15 mmoles) of the protected tripeptide prepared according to Step 3 of Example 7 are converted into the active ester according to the method of Step 5 of Example 2, with the difference that the product is purified by trituration with ether. 10.3 g (98%) of tert.-butoxycarbonyl-L-tyrosyl-D-norleucyl-glycine pentachlorophenyl ester are obtained; m.p.: 175°–177° C., $R_f^{12}=0.5$–$0.6$.

Step 2:
tert.-Butoxycarbonyl-L-tyrosyl-D-norleucyl-glycyl-L-phenylalanyl-L-α-aminopentanesulfonic acid N-methylmorpholine salt 2.2 g (3.15 mmoles) of the protected tripeptide ester obtained in Step 1 above are condensed with 0.95 g (3 mmoles) of the dipeptide prepared according to Step 4 of Example 2. The reaction is performed as described in Step 6 of Example 2 to obtain 1.63 g (64%) of tert.-butoxycarbonyl-L-tyrosyl-D-norleucyl-glycyl-L-phenylalanyl-L-α-aminopentanesulfonic acid N-methylmorpholine salt; m.p.: 134°–135° C., $R_f^5=0.6$–$0.7$, $[\alpha]_D^{20}=-18.8°$ (c=1%, in dimethyl formamide).

Step 3:
L-Tyrosyl-D-norleucyl-glycyl-L-phenylalanyl-L-α-aminopentanesulfonic acid 1.5 g (1.75 mmoles) of the protected pentapeptide salt obtained in Step 2 above are processed further as described in Step 7 of Example 2 with the difference that the precipitate is also washed with 10 ml of water. 0.91 g (80%) of L-tyrosyl-D-norleucyl-glycyl-L-phenylalanyl-L-α-aminopentanesulfonic acid are obtained; m.p.: 198°–200° C., $R_f^6=0.33$–$0.43$, $[\alpha]_D^{20}=-12.1°$ (c=1%, in methanol).

EXAMPLE 9

Preparation of
L-tyrosyl-D-norleucyl-glycyl-L-phenylalanyl-L-α-amino-γ-methyl-butanesulfonic acid

Step 1: DL-α-Amino-γ-methyl-butanesulfonic acid

One proceeds as described in Step 1 of Example 2 with the difference that 63.5 ml (510 mmoles) of isovaleraldehyde are used as starting substance. 40 g (47.7%) of DL-α-amino-γ-methyl-butanesulfonic acid are obtained; m.p.: 142°–144° C.

Step 2:
Benzyloxycarbonyl-L-phenylalanyl-DL-α-amino-γ-methyl-butanesulfonic acid 33 g (110 mmoles) of benzyloxycarbonyl-L-phenylalanine and 12.2 ml (110 mmoles) of N-methylmorpholine are dissolved in 200 ml of dimethyl formamide. The solution is cooled to −10° C., and 14.5 ml (110 mmoles) of isobutyl chloroformate are added to the stirred solution at this temperature. After 10 minutes of stirring a solution of 16.7 g (100 mmoles) of DL-α-amino-γ-methyl-butanesulfonic acid obtained in Step 1 above and 14 ml (100 mmoles) of triethyl amine in 200 ml of dimethyl formamide is added. The reaction mixture is stirred at −10° C. for one hour and then at 0° C. for 4 hours, and evaporated under reduced pressure. The residue is dissolved in 500 ml of water, the solution is washed thrice with 100 ml of diethyl ether, each, acidified to pH=2 with concentrated aqueous hydrochloric acid, and extracted thrice with 100 ml of n-butanol saturated with water, each. The n-butanol solutions are combined, washed twice with 50 ml of water saturated with n-butanol, each, and evaporated under reduced pressure. 27 g (85%) of benzyloxycarbonyl-L-phenylalanyl-DL-α-amino-γ-methyl-butanesulfonic acid are obtained; $R_f^3=0.20$–$0.30$.

Step 3:
L-Phenylalanyl-D-α-amino-γ-methyl-butanesulfonic acid 27 g (85.87 mmoles) of the protected dipeptide obtained in Step 2 above are dissolved in a mixture of 600 ml of methanol and 60 ml of 25% aqueous ammonia, and the mixture is hydrogenated in the presence of palladium-on-carbon catalyst. At the end of the reaction the catalyst is filtered off and washed with 50% aqueous methanol. The filtrate and the wash are combined and evaporated under reduced pressure. The residue is dried in a vacuum desiccator over concentrated sulfuric acid, then stirred with 50 ml of warm (60°–80° C.) water. The crystal suspension is allowed to stand at about 5° C. overnight, then the solid is filtered off and washed thrice with 5 ml of cold water, each. The filtrate and the wash are combined and stored for further processing (see Step 4). The crystalline substance is dried in a vacuum desiccator. 10.8 g (34.35 mmoles), 80%) of L-phenylalanyl-D-α-amino-γ-methyl-butanesulfonic acid are obtained; m.p.: 254°–256° C., $[\alpha]_D^{20}=+127.0°$ (c=1%, in 1 n aqueous sodium hydroxide solution).

Step 4:
L-Phenylalanyl-L-α-amino-γ-methyl-butanesulfonic acid

The mother liquor of crystallization obtained in Step 3 above is evaporated to dryness under reduced pressure. The residue is triturated with tetrahydrofuran, the solid is filtered off, washed with tetrahydrofuran and dried. 10.1 g (32.2 mmoles, 75%) of L-phenylalanyl-L-α-amino-γ-methylbutanesulfonic acid are obtained; m.p.: 226°–228° C., $[\alpha]_D^{20}=-77.85°$ (c=1%, in 1 n aqueous sodium hydroxide solution).

Step 5:
L-Tyrosyl-D-norleucyl-glycyl-L-phenylalanyl-L-α-amino-γ-methyl-butanesulfonic acid 1.08 g (2.4 mmoles) of tert.-butoxycarbonyl-L-tyrosyl-D-norleucyl-glycine, obtained as described in Step 3 of Example 7, are condensed with 0.64 g (2 mmoles) of L-phenylalanyl-L-α-amino-γ-methyl-butanesulfonic acid obtained in Step 4 above. The reaction is performed as described in Step 7 of Example 1. The residue obtained after evaporating the reaction mixture is dissolved in 30 ml of water, the solution is washed thrice with 10 ml of ethyl acetate, each, the ethyl acetate solutions are combined and extracted twice with 5 ml of water, each. The aqueous solutions are combined, acidified to pH=2 with 1 n aqueous sulfuric acid, and extracted thrice with 10 ml of a 2:1 mixture of ethyl acetate and n-butanol, each. The organic solutions are combined, washed twice with 5 ml of water saturated with butanol, each, and evaporated under reduced pressure. The residue is dissolved in 10 ml of trifluoroacetic acid, and the solution is allowed to stand for 30 minutes. The solution is evaporated under reduced pressure, the residue is triturated with ether, the solid is filtered off, washed with ether and dried. 0.9 g (80%) of L-tyrosyl-D-norleucyl-glycyl-L-phenylalanyl-L-$\alpha$-amino-$\gamma$-methyl-butanesulfonic acid are obtained; m.p.: 199°–200° C., $[\alpha]_D^{20}=+1.0°$ (c=1%, in 1 n aqueous sodium hydroxide solution), $R_f^5=0.50$–0.60.

EXAMPLE 10

Preparation of
L-tyrosyl-glycyl-glycyl-L-phenylalanyl-D-$\alpha$-aminopentanesulfonic acid Step 1:
tert.-Butoxycarbonyl-L-tyrosyl-glycyl-glycyl-L-phenylalanyl-D-$\alpha$-aminopentanesulfonic acid N-methylmorpholine salt One proceeds as described in Step 6 of Example 2 with the difference that 0.95 g (3 mmoles) of the dipeptide prepared according to Step 3 of Example 2 and 2.0 g (3.15 mmoles) of the protected tripeptide ester prepared according to Step 5 of Example 2 are applied as starting substances. 2.2 g (92.5%) of tert.-butoxycarbonyl-L-tyrosyl-glycyl-glycyl-L-phenylalanyl-D-$\alpha$-aminopentanesulfonic acid N-methylmorpholine salt are obtained; m.p.: 133° C., $R_f^7=0.23$–0.33, $[\alpha]_D^{20}=-16.6°$ (c=1%, in dimethyl formamide).

Step 2:
L-Tyrosyl-glycyl-glycyl-L-phenylalanyl-D-$\alpha$-aminopentanesulfonic acid 1.4 g (1.75 mmoles) of the protected pentapeptide salt obtained in Step 1 above is processed further as described in Step 7 of Example 2 to obtain 1.0 g (98%) of L-tyrosyl-glycyl-glycyl-L-phenylalanyl-D-$\alpha$-aminopentanesulfonic acid; m.p.: 192°–194° C., $R_f^5=0.20$–0.35, $R_f^8=0.35$–0.45, $[\alpha]_D^{20}=+6.01°$ (c=1%, in 90% acetic acid).

EXAMPLE 11

Preparation of
L-tyrosyl-D-alanyl-glycyl-L-phenylalanyl-D-$\alpha$-aminopentanesulfonic acid Step 1:
tert.-Butoxycarbonyl-L-tyrosyl-D-alanyl-glycyl-L-phenylalanyl-D-$\alpha$-aminopentanesulfonic acid triethylamine salt One proceeds as described in Step 6 of Example 2 with the difference that 0.95 g (3 mmoles) of the dipeptide obtained according to Step 3 of Example 2 and 2.1 g (3.15 mmoles) of the tripeptide ester obtained according to Step 1 of Example 4 are condensed, and 0.4 ml and 0.45 ml of triethylamine are applied as tertiary base. 2.40 g (99%) of tert.-butoxycarbonyl-L-tyrosyl-D-alanyl-glycyl-L-phenylalanyl-D-$\alpha$-aminopentanesulfonic acid triethylamine salt are obtained; m.p.: 123°–124° C., $R^5=0.4$–0.5, $[\alpha]^{20}=-29.9°$ (c=1%, in dimethyl formamide).

Step 2:
L-Tyrosyl-D-alanyl-glycyl-L-phenylalanyl-D-$\alpha$-aminopentanesulfonic acid 1.4 g (1.75 mmoles) of the protected pentapeptide salt obtained in Step 1 above are processed further as described in Step 7 of Example 2, with the difference that the precipitate is also washed with 10 ml of water. 0.78 g (73.3%) of L-tyrosyl-D-alanyl-glycyl-L-phenylalanyl-D-$\alpha$-aminopentanesulfonic acid are obtained; m.p.: 262°–264° C., $R_f^7=0.3$–0.4, $[\alpha]_D^{20}=+25.4°$ (c=1%, in 80% acetic acid).

EXAMPLE 12

Preparation of
L-tyrosyl-D-methionyl-glycyl-L-phenylalanyl-D-$\alpha$-aminopentanesulfonic acid Step 1:
tert.-Butoxycarbonyl-L-tyrosyl-D-methionyl-glycyl-L-phenylalanyl-D-$\alpha$-aminopentanesulfonic acid N-methylmorpholine salt.

One proceeds as described in Step 6 of Example 2 with the difference that 0.95 g (3 mmoles) of the dipeptide obtained according to Step 3 of Example 2 and 2.25 g (3.15 mmoles) of the protected tripeptide ester obtained according to Step 1 of Example 6 are condensed. 1.96 g (74.6%) of tert.-butoxycarbonyl-L-tyrosyl-D-methionyl-glycyl-L-phenylalanine-D-$\alpha$-aminopentanesulfonic acid N-methylmorpholine salt are obtained; m.p.: 125°–127° C., $R_f^5=0.45$–0.55, $[\alpha]_D^{20}=-14.6°$ (c=1%, in dimethyl formamide).

Step 2:
L-Tyrosyl-D-methionyl-glycyl-L-phenylalanyl-D-$\alpha$-aminopentanesulfonic acid 1.52 g (1.75 mmoles) of the protected pentapeptide salt obtained in Step 1 above are processed further as described in Step 3 of Example 6. 0.9 g (73.3%) of L-tyrosyl-D-methionyl-glycyl-L-phenylalanyl-D-$\alpha$-aminopentanesulfonic acid are obtained; m.p.: 262°–264° C., $R_f^6=0.1$–0.2, $R_f^5=0.35$–0.45, $[\alpha]_D^{20}=+26.8°$ (c=1%, in trifluoroacetic acid).

EXAMPLE 13

Preparation of
L-tyrosyl-D-norleucyl-glycyl-L-phenylalanyl-D-$\alpha$-aminopentanesulfonic acid Step 1:
tert.-Butoxycarbonyl-L-tyrosyl-D-norleucyl-glycyl-L-phenylalanyl-D-$\alpha$-aminopentanesulfonic acid N-methylmorpholine salt One proceeds as described in Step 6 of Example 2 with the difference that 0.95 g (3 mmoles) of the dipeptide prepared according to Step 3 of Example 2 are condensed with 2.2 g (3.15 mmoles) of the protected tripeptide ester prepared according to Step 1 of Example 8. 1.9 g (75%) of tert.-butoxycarbonyl-L-tyrosyl-D-norleucyl-glycyl-L-phenylalanyl-D-$\alpha$-aminopentanesulfonic acid N-methylmorpholine salt are obtained; m.p.: 132°–133° C., $R_f^5=0.7$–0.8, $[\alpha]_D^{20}=-15.6°$ (c=1%, in dimethyl formamide).

Step 2:
L-Tyrosyl-D-norleucyl-glycyl-L-phenylalanyl-D-$\alpha$-aminopentanesulfonic acid 1.5 g (1.75 mmoles) of the protected pentapeptide salt obtained in Step 1 above are processed further as described in Step 3 of Example 6 to obtain 1.02 g of L-tyrosyl-D-norleucyl-glycyl-L-phenylalanyl-D-$\alpha$-aminopentanesulfonic acid; m.p.: 257° C., $R_f^6=0.4$–0.5, $[\alpha]_D^{20}=+3°$ (c=1%, in trifluoroacetic acid); yield: 90%.

EXAMPLE 14

Preparation of
L-tyrosyl-D-methionyl-glycyl-L-phenylalanyl-D-α-aminopentanephosphonic acid One proceeds as described in Step 7 of Example 1 with the difference that 1.13 g (2.4 mmoles) of tert.-butoxycarbonyl-L-tyrosyl-D-methionyl-glycine, prepared according to Step 2 of Example 5, and 0.63 g (2 mmoles) of L-phenylalanyl-D-α-aminopentanephosphonic acid, prepared according to Step 3 of Example 1, are used as starting substances. 0.9 g (70%) of L-tyrosyl-D-methionyl-glycyl-L-phenylalanyl-D-α-aminopentanephosphonic acid are obtained; m.p.: 262°–265° C., $[\alpha]_D^{20}= +59.2°$ (c=1%, in 1 n sodium hydroxide solution), $R_f^5=0.35-0.40$.

EXAMPLE 15

Preparation of
L-tyrosyl-D-norleucyl-glycyl-L-phenylalanyl-D-α-amino-γ-methyl-butanesulfonic acid One proceeds as described in Step 5 of Example 10 with the difference that 1.08 g (2.4 mmoles) of tert.-butoxycarbonyl-L-tyrosyl-D-norleucyl-glycine, prepared according to Step 3 of Example 7, and 0.64 g (2 mmoles) of D-α-amino-γ-methyl-butanesulfonic acid, prepared according to Step 3 of Example 9, are used as starting substances. 0.95 g (84%) of L-tyrosyl-D-norleucyl-glycyl-L-phenylalanyl-D-α-amino-γ-methyl-butanesulfonic acid are obtained; m.p.: 187°–190° C., $[\alpha]_D^{20}= +58.9°$ (c=1%, in 1 n aqueous sodium hydroxide solution).

EXAMPLE 16

Preparation of
L-tyrosyl-D-phenylalanyl-glycyl-L-phenylalanyl-L-α-aminopentanesulfonic acid Step 1: tert.-Butoxycarbonyl-D-phenylalanyl-glycine benzyl ester 13.3 g (50 mmoles) of tert.-butoxycarbonyl-D-phenylalanine and 5.6 ml (50 mmoles) of N-methylmorpholine are dissolved in 50 ml of dimethyl formamide. The solution is cooled to −10° C., and 6.6 ml (50 mmoles) of isobutyl chloroformate are added with stirring. After 10 minutes the mixture is cooled to −20° C., and a solution of 18.6 g (55 mmoles) of glycine benzyl ester p-toluenesulfonate and 6.1 ml (55 mmoles) of N-methylmorpholine in 80 ml of dimethyl formamide, cooled to −20° C., is added. The reaction mixture is stirred at −10° C. for 10 minutes, at 0° C. for one hour, and then at room temperature overnight. The mixture is filtered and evaporated under reduced pressure. The residue is dissolved in a mixture of 300 ml of ethyl acetate and 100 ml of water. The ethyl acetate phase is separated and washed successively with 5% aqueous sodium hydrocarbonate solution (2×60 ml), water (2×60 ml), 1 n aqueous hydrochloric acid cooled with ice water (2×60 ml) and with water (2×60 ml) again, dried over sodium sulfate, decolourized with carbon, filtered, and the filtrate is evaporated under reduced pressure. The crystalline residue is suspended in a 1:1 mixture of diethyl ether and n-hexane, the solid is filtered off, washed with the above solvent mixture and dried in a vacuum desiccator. 18.95 g (91.9%) of tert.-butoxycarbonyl-D-phenylalanyl-glycine benzyl ester are obtained; m.p.: 133°–134° C., $R_f^{14}=0.28-0.38$, $[\alpha]_D^{20}= +8°$ (c=1%, in dimethyl formamide).

Step 2:
tert.-Butoxycarbonyl-L-tyrosyl-D-phenylalanyl-glycine benzyl ester 18.55 g (45 mmoles) of the protected dipeptide ester obtained in Step 1 above are dissolved in 60 ml of ethyl acetate containing 11–15% of hydrochloric acid. After 0.5 hours of standing the solution is evaporated, and the residue is dried in a vacuum desiccator above potassium hydroxide. The resulting substance, $R_f^3=0.4-0.5$, is dissolved in 40 ml of dimethyl formamide, and 5.0 ml (45 mmoles) of N-methylmorpholine and 26.2 g (49.5 mmoles) of tert.-butoxycarbonyl-L-tyrosine pentachlorophenyl ester are added. The reaction mixture is stirred for 16–20 hours. During the first two hours 5.5 ml (49.5 mmoles) of N-methylmorpholine are added to the mixture in five portions. The reaction mixture is evaporated under reduced pressure, the residue is dissolved in a mixture of 300 ml of ethyl acetate and 50 ml of water, the ethyl acetate phase is separated, washed twice with 50 ml of 1 n aqueous hydrochloric acid cooled with ice water and then twice with 50 ml of water, each, dried over sodium sulfate, decolourized with carbon, filtered, and the filtrate is evaporated under reduced pressure. The crystalline residue is suspended in diisopropyl ether, the solid is filtered off, washed with diisopropyl ether, and dried in a vacuum desiccator. 23.5 g (90.8%) of tert.-butoxycarbonyl-L-tyrosyl-D-phenylalanyl-glycine benzyl ester are obtained; m.p.: 169° C., $R_f^{10}=0.45-0.55$, $[\alpha]_D^{20}$ +16.3° (c=1%, in dimethyl formamide).

Step 3:
tert.-Butoxycarbonyl-L-tyrosyl-D-phenylalanyl-glycine 23.0 g (40 mmoles) of the protected tripeptide ester obtained in Step 2 above are dissolved in 40 ml of methanol, and the mixture is hydrogenated in the presence of palladium-on-carbon catalyst. At the end of the reaction the catalyst is filtered off, washed with methanol, the filtrate and the wash are combined and evaporated under reduced pressure. The residue is triturated with diethyl ether, the solid is filtered off, washed with diethyl ether and dried in a vacuum desiccator. 17.45 g (89.8%) of tert.-butoxycarbonyl-L-tyrosyl-D-phenylalanyl-glycine are obtained; m.p.: 105°–110° C., $R_f^{13}=0.2-0.3$.

Step 4:
tert.-Butoxycarbonyl-L-tyrosyl-D-phenylalanyl-glycine pentachlorophenyl ester 7.3 g (15 mmoles) of the protected tripeptide obtained in Step 3 above are converted into the active ester as described in Step 5 of Example 2. 9.68 g (87.9%) of tert.-butoxycarbonyl-L-tyrosyl-D-phenylalanyl-glycine pentachlorophenyl ester are obtained; m.p.: 209°210° C., $R_f^{12}=0.6-0.7$, $[\alpha]_D^{20}= +15.4°$ (c=1%, in dimethyl formamide).

Step 5:
tert.-Butoxycarbonyl-L-tyrosyl-D-phenylalanyl-glycyl-L-phenylalanyl-L-α-aminopentanesulfonic acid N-methylmorpholine salt One proceeds as described in Step 6 of Example 2 with the difference that 2.3 g (3.15 mmoles) of the protected tripeptide ester obtained in Step 4 above and 0.95 g (3 mmoles) of the dipeptide obtained according to Step 4 of Example 2 are applied as starting substances. 1.87 g (70.6%) of tert.-butoxycarbonyl-L-tyrosyl-D-phenylalanyl-glycyl-L-phenylalanyl-L-α-aminopentanesulfonic acid N-methylmorpholine salt are obtained; m.p.: 130°–132° C., $R_f^4$=0.3–0.4, $[\alpha]_D^{20}$=−12.3° (c=1%, in dimethyl formamide).

Step 6:
L-Tyrosyl-D-phenylalanyl-glycyl-L-phenylalanyl-L-α-aminopentanesulfonic acid 1.55 g (1.75 mmoles) of the protected pentapeptide obtained in Step 5 above are processed further as described in Step 7 of Example 2 to obtain 1.08 g (90.8%) of L-tyrosyl-D-phenylalanyl-glycyl-L-phenylalanyl-L-α-aminopentanesulfonic acid; m.p.: 198°–204° C., $R_f^6$=0.6–0.7, $R_f^8$=0.8–0.9, $[\alpha]_D^{20}$=−43° (c=1%, in trifluoroacetic acid).

EXAMPLE 17

Preparation of
L-tyrosyl-D-phenylalanyl-glycyl-L-phenylalanyl-D-α-aminopentanesulfonic acid Step 1:
tert.-Butoxycarbonyl-L-tyrosyl-D-phenylalanyl-glycyl-L-phenylalanyl-D-α-aminopentanesulfonic acid N-methylmorpholine salt One proceeds as described in Step 6 of Example 2 with the difference that 0.95 g (3 mmoles) of the dipeptide obtained according to Step 3 of Example 2 and 2.3 g (3.15 mmoles) of the protected tripeptide ester obtained according to Step 4 of Example 16 are applied as starting substances. 2.45 g (92.5%) of tert.-butoxycarbonyl-L-tyrosyl-D-phenylalanyl-glycyl-L-phenylalanyl-D-α-aminopentanesulfonic acid N-methylmorpholine salt are obtained; m.p.: 134°–135° C., $R_f^3$=0.27–0.37, $[\alpha]_D^{20}$=−6.05° (c=1%, in dimethyl formamide).

Step 2:
L-Tyrosyl-D-phenylalanyl-glycyl-L-phenylalanyl-D-α-aminopentanesulfonic acid 1.55 g (1.75 mmoles) of the protected pentapeptide salt obtained in Step 1 above are processed further as described in Step 7 of Example 2 to obtain 1.09 g (91.2%) of L-tyrosyl-D-phenylalanyl-glycyl-L-phenylalanyl-D-α-aminopentanesulfonic acid; m.p.: 250° C., $R_f^6$=0.7–0.8, $R_f^7$=0.8–0.9, $[\alpha]_D^{20}$=−13.1° (c=1%, in trifluoroacetic acid).

EXAMPLE 18

Preparation of
L-tyrosyl-D-norleucyl-glycyl-L-phenylalanyl-L-α-aminopentanephosphonic acid copper salt 130 mg (0.2 mmoles) of the pentapeptide obtained as described in Step 4 of Example 7 are dissolved in 4 ml of 0.1 N sodium hydroxide, and 60 mg (0.24 mmoles) of copper sulfate pentahydrate dissolved in 1 ml of water are added. The separated substance is filtered off, washed with water (3×1 ml) and dried in a vacuum desiccator. 127 mg (90%) of L-tyrosyl-D-norleucyl-glycyl-L-phenylalanyl-L-α-aminopentanephosphonic acid copper salt are obtained; m.p.: >260° C.

Analysis: Calculated for $C_{31}H_{44}O_8N_5PCu$ (M.wt.: 709.2); N: 9.87%, Cu: 8.96%; Found: N: 9.7%, Cu: 9.0%.

EXAMPLE 19

Preparation of
L-tyrosyl-D-norleucyl-glycyl-L-phenylalanyl-L-α-aminopentanephosphonic acid zinc salt 130 mg (0.2 mmoles) of the pentapeptide obtained as described in Step 4 of Example 7 are dissolved in 4 ml of 0.1 N sodium hydroxide, and 53 mg (0.24 mmoles) of zinc acetate dihydrate dissolved in 1 ml of water are added. The separated substance is filtered off, washed with water (3×1 ml) and dried in a vacuum desiccator. 128 mg (90%) of L-tyrosyl-D-norleucyl-glycyl-L-phenylalanyl-L-α-aminopentanephosphonic acid zinc salt are obtained; m.p.: >260° C.

Analysis: Calculated for $C_{31}H_{44}O_8N_5PZn$ (M.wt.: 711.1); N: 9.85%, Zn: 9.19%; Found: N: 9.8%, Zn: 9.05%

EXAMPLE 20

Preparation of
L-tyrosyl-D-norleucyl-glycyl-L-phenylalanyl-L-α-aminopentanesulfonic acid zinc salt 130 mg (0.2 mmoles) of the pentapeptide obtained as described in Step 3 of Example 8 are dissolved in 2 ml of 0.1 N sodium hydroxide, and 44 mg (2.0 mmoles) of zinc acetate dihydrate dissolved in 1 ml of water are added. After cooling in an ice bath for 2 hours the separated substance is filtered off, washed with cold water (3×1 ml) and dried in a vacuum desiccator. 116 mg (85%) of L-tyrosyl-L-norleucyl-glycyl-L-phenylalanyl-L-α-aminopentanesulfonic acid zinc salt are obtained; m.p.: 215°–219° C.

Analysis: Calculated for $C_{31}H_{44}O_8N_5SZn$ (M.wt.: 712.15); N: 9.83%, Zn: 9.18%; Found: N: 10.0%, Zn: 9.1%.

What we claim is:
1. An new enkephalin analog of the formula (I),

Tyr-X-Gly-Phe-Y            (I)

wherein
Tyr, Gly and Phe represent L-tyrosyl, glycyl and L-phenylalanyl residues, respectively,
X is a glycyl group or a D-α-aminocarboxylic acid residue with a lower alkyl, lower thioalkyl or phenyl-(lower)-alkyl side chain, and
Y is the residue of an L, D or DL-α-aminophosphonic acid or L, D or DL-α-aminosulfonic acid, each having a lower alkyl side chain,
or a salt thereof.
2. A hypotensive composition comprising an effective amount of an enkephalin analog of the formula (I), as defined in claim 1, or a pharmaceutically acceptable salt thereof with a pharmaceutically acceptable inert carrier.
3. A compound as defined in claim 1 wherein X is D-Ala, Gly, D-Met, D-NLe, or D-Phe and Y is an α-aminobutane or α-aminopentane phosphonic or sulfonic acid or a copper or zinc salt thereof.
4. The compound defined in claim 3 and selected from the group which consists of:
Tyr-D-NLe-Gly-Phe-α-aminopentane sulfonic acid,
Tyr-D-NLe-Gly-Phe-α-aminopentane phosphonic acid,
Tyr-D-Phe-Gly-Phe-α-aminopentane sulfonic acid,
Tyr-D-NLe-Gly-Phe-α-amino-γ-methylbutane sulfonic acid, Tyr-D-Met-Gly-Phe-α-aminopentane phosphonic acid,
Tyr-D-Met-Gly-Phe-α-aminopentane sulfonic acid,
Tyr-D-Ala-Gly-Phe-α-aminopentane sulfonic acid,
Tyr-Gly-Gly-Phe-α-aminopentane sulfonic acid,
Tyr-D-Ala-Gly-Phe-α-aminopentane phosphonic acid, and
Tyr-Gly-Gly-Phe-α-aminopentane phosphonic acid, or a copper or zinc salt thereof.

* * * * *